United States Patent [19]

Kirsch et al.

[11] Patent Number: 4,791,657

[45] Date of Patent: Dec. 13, 1988

[54] INTRAORAL RADIOGRAPHIC FILM PACKET

[76] Inventors: Alan Kirsch, 1080 Squirrel Rd., Jenkintown, Pa. 19046; Shirley Feinstein, 825 Warfield La., Huntingdon Valley, Pa. 19006

[21] Appl. No.: 117,808

[22] Filed: Nov. 6, 1987

[51] Int. Cl.[4] .......... A61B 6/14

[52] U.S. Cl. .......... 378/169; 378/168; 378/184

[58] Field of Search .......... 378/38, 167, 168, 169, 378/184

[56] References Cited

U.S. PATENT DOCUMENTS

| | | | |
|---|---|---|---|
| 1,537,925 | 6/1925 | Bolin | 378/169 |
| 1,564,269 | 12/1925 | Peyser | 378/169 |
| 2,084,092 | 6/1937 | Kenney | 378/168 |
| 3,168,647 | 2/1965 | Kollock | 378/184 |
| 4,626,216 | 12/1986 | Strong-Grainger | 378/168 |

*Primary Examiner*—Carolyn E. Fields
*Assistant Examiner*—David P. Porta
*Attorney, Agent, or Firm*—Gregory J. Gore

[57] ABSTRACT

A dental radiographic film packet includes soft corners for greater patient comfort. Corner areas contain additional air space to permit additional flexing of the film chip in these areas. Furthermore, other internal structures, such as cardboard elements, have been removed to increase flexibility in these areas. The outer surface of the film packet is seamless at the corners to eliminate any sharp edges.

2 Claims, 1 Drawing Sheet

FIG. 1
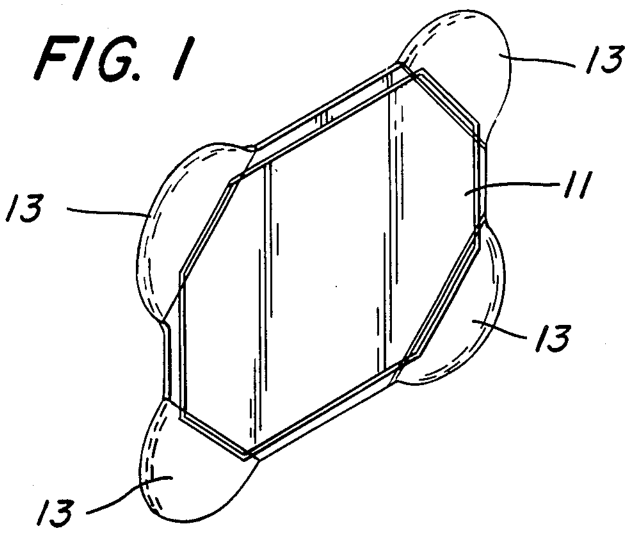
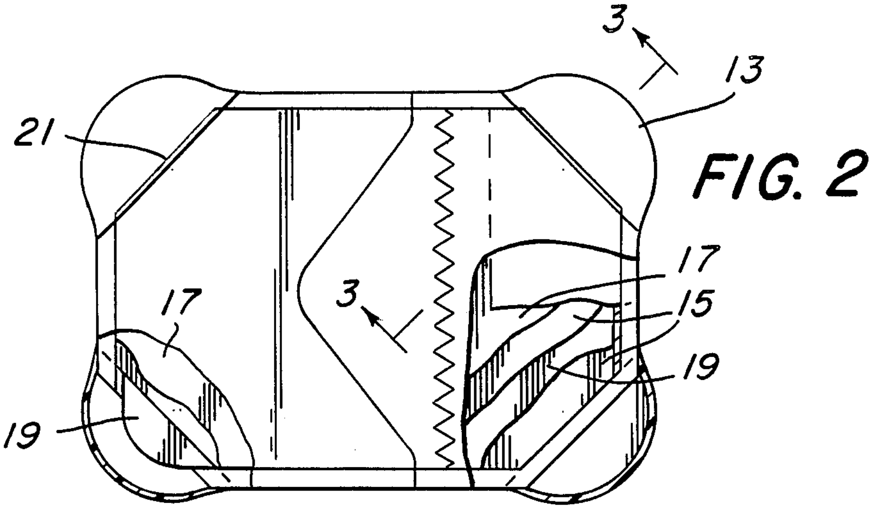
FIG. 2
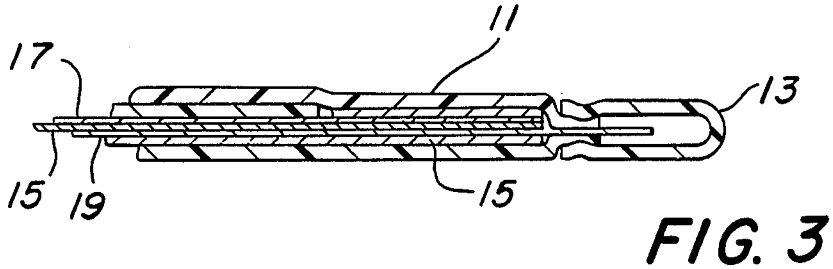
FIG. 3

INTRAORAL RADIOGRAPHIC FILM PACKET

FIELD OF THE INVENTION

The present device relates to intraoral X-ray film packets for use in dentistry.

BACKGROUND OF THE INVENTION

The technique of "paralleling" in dental radiology has been shown to be a superior technique which yields low distortion exposures if the film packet can be adequately placed in the patient's oral cavity. However, it is well-known that achieving proper radiographic exposures, especially using this technique, results in a great degree of patient discomfort. Patients often experience intense pain created by the sharp edges of the radiographic film packet when it is pressed tightly against intraoral tissues in order to achieve a proper exposure.

This problem has been recognized by many in the field of dental radiographic science as disclosed in U.S. Pat. No. 4,626,216 to Strong-Grainger which provides an extensive discussion of this problem and the prior art. The Strong-Grainger solution to this problem is to include additional padding around the edges of the normal X-ray film packet. The padding completely covers the sharp, heat-sealed edge of the most commonly used plastic jacket-type radiographic film packet and is reported to increase patient comfort during radiographic examination. This padding, however, greatly increases the bulk and dimension of the film packet and therefore it does not present the opportunity for best use and greatest spatial coverage of the X-ray film. The present design represents an improvement in the art in order to achieve greater patient comfort during X-ray examination without limiting the X-ray procedure.

SUMMARY OF THE INVENTION

It has been discovered that in most instances, the corners of the film packet are bent and deflected when forced into irregular areas of the mouth. In order to overcome the problems described above, the present device provides patient comfort by reducing the stiffness of the film packet at the corners which have been shown to be the critical points at which the film packet presses into the patient's oral tissues thus causing discomfort.

Prior art film packets resist deflection at the corners due to the rigidity of the structure. Also, it has been found that the multilayer construction of the film packet resists deflection merely by its multilayer structure in combination with a tightly fitting outer jacket around all four corners. Lastly, it has been observed that the sharp seam edge around the periphery of the standard plastic cover film packet causes the most patient discomfort.

The present invention includes the removal of all elements of the film packet at the corner areas except the film chip itself. This reduces stiffness at the corners. The plastic jacket is removed from each of the corners and four corner covers added. Each corner cover extends beyond the dimension of the film chip and does not restrict its deformation, unlike prior art film packet corners which tightly restrict chip movement and thus promote added rigidity. The corner covers are seamless pockets which have a smooth contour without a sharp seam or edge.

BRIEF DESCRIPTION OF THE DRAWINGS

FIG. 1 is an isometric view of the present device showing various features of the invention.

FIG. 2 is a partial front sectional view.

FIG. 3 is a sectional view taken from FIG. 2 as indicated.

DESCRIPTION OF THE PREFERRED EMBODIMENT

Referring now to FIG. 1, the present device is shown with corner covers 13 encasing the four corners of the standard-type plastic film packet 11.

Referring now to FIG. 2, standard plastic jacket radiographic film packets such as the type manufactured by Kodak(R) Company contain many layers of internal components within the plastic outer covering 11. Stiff cardboard 15 and metal foil 17 together with centrally positioned film chip 19 comprise the internal components. As shown in FIG. 2, all internal components, except film chip 19, are removed in the corner areas along an approximately 45 degree line 21 at each corner. As further shown in FIG. 3, this not only removes material from the corner areas but creates an air space at the corners around the edge of the film chip both laterally and longitudinally.

Referring further to FIG. 3, corner covers 13 have a smooth outer contour without any sharp seams. The additional space between the outer edge and the film chip is sufficient so that when the corner portion is deflected, the side surfaces of the corners can slide against the film and therefore not restrict deformation or bending of the film chip. In this way, the covering does not add to the rigidity of the film packet construction.

By these structural relations, the corner areas of the film packet are extrexely flexible and without any sharp edges. The corners are as flexible as the film. Furthermore, the outside dimensions of the film packet have only been increased very slightly and the thickness of the packet has not been increased at all. This provides the required comfort, together with a compact design, which is a combination heretofore unachieved by the prior art.

It should be understood that the above description discloses specific embodiments of the present invention and are for purposes of illustration only. There may be other modifications and changes obvious to those of ordinary skill in the art which fall within the scope of the present invention which should be limited only by the following claims and their legal equivalents.

What is claimed is:

1. An intraoral X-ray film packet for use in dentistry, comprising:

a. an outer jacket, b. a substantially rectangular X-ray film chip located within said jacket, c. four corner covers affixed to said jacket enclosing each of the four corners of said film chip, said corner covers including a substantial air space, both latitudinally and longitudinally around the film chip, and d. said film chip being the only element within each corner cover.

2. The X-ray film packet of claim 1 further described in that said corner covers are seamless.

* * * * *